United States Patent [19]
Imran

[11] Patent Number: 5,396,887
[45] Date of Patent: Mar. 14, 1995

[54] APPARATUS AND METHOD FOR DETECTING CONTACT PRESSURE

[75] Inventor: Mir A. Imran, Palo Alto, Calif.

[73] Assignee: Cardiac Pathways Corporation, Sunnyvale, Calif.

[21] Appl. No.: 126,045

[22] Filed: Sep. 23, 1993

[51] Int. Cl.⁶ ............................................. A61B 5/04
[52] U.S. Cl. ................... 128/642; 128/774; 607/119
[58] Field of Search ............... 128/774, 642; 606/40, 606/46; 607/119, 122, 154

[56] References Cited

U.S. PATENT DOCUMENTS

| | | |
|---|---|---|
| 4,543,965 | 10/1985 | Pack et al. ........................... 128/774 |
| 5,083,573 | 1/1992 | Arns ................................... 128/774 |
| 5,156,151 | 10/1992 | Imran . | |
| 5,224,469 | 7/1993 | Mocny ................................ 128/774 |
| 5,293,868 | 3/1994 | Nardelli ............................. 607/119 |

*Primary Examiner*—Max Hindenburg
*Attorney, Agent, or Firm*—Flehr, Hohbach, Test, Albritton & Herbert

[57] ABSTRACT

An apparatus for performing an operation inside a body in the vicinity of a wall therein which includes a flexible elongate member having proximal and distal extremities. The distal extremity is adapted to be inserted into the body for performing the operation therein and the proximal extremity is adapted to be disposed outside the body. A pressure sensor is carried by the distal extremity of the flexible elongate tubular member for sensing the force being applied to the distal extremity in bringing it into engagement with the wall so that the force being applied to the distal extremity can be controlled.

12 Claims, 1 Drawing Sheet

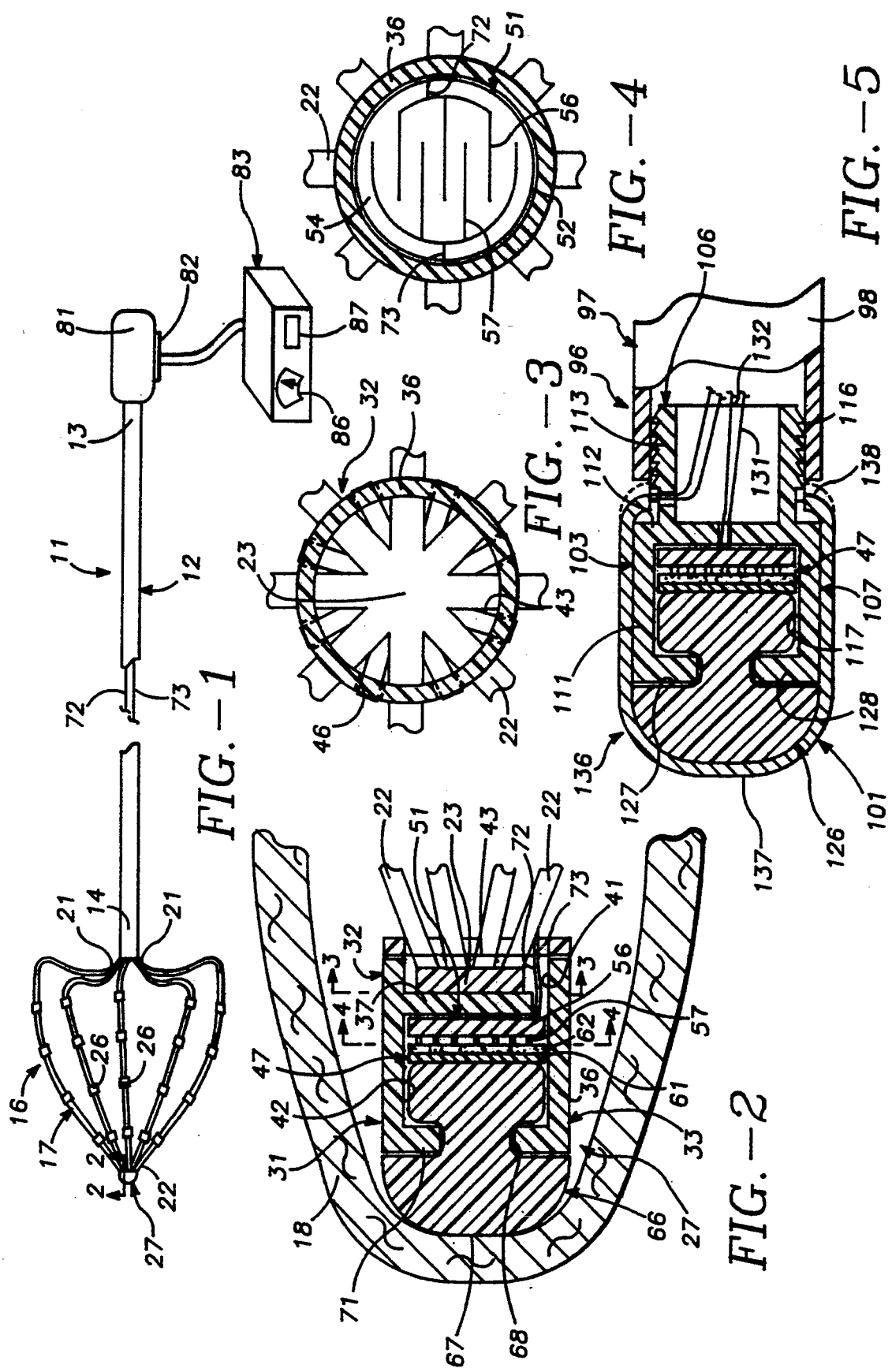

APPARATUS AND METHOD FOR DETECTING CONTACT PRESSURE

BACKGROUND OF THE INVENTION

1. Field of the Invention

This invention pertains generally to medical devices and, more particularly, to medical devices with a pressure sensor on the distal extremity thereof.

2. Description of the Related Art

Many medical devices operate on the wall of a vessel in a body. For example, devices having expandable assemblies on the distal extremity thereof have been provided for mapping and/or ablating the wall in a chamber of the heart. It has been found that if the operating physician is not careful, these devices can be pushed harder or further into the body than desired to damage or even penetrate the heart wall. In addition, it has been found to be difficult when performing ablations with these devices to monitor the contact pressure exerted by the ablation electrode against the targeted tissue of the heart wall. Because of the foregoing, there is a need for a new and improved apparatus which overcomes the above named disadvantages.

OBJECTS OF THE INVENTION

In general, it is an object of the present invention to provide a medical device and a method in which the amount of force being exerted by the distal extremity of the device against a wall within the body can be sensed.

Another object of the invention is to provide a device and method of the above character in which the axial force of an endocardial mapping device can be monitored.

Another object of the invention is to provide a device and method of the above character in which a desired minimum pressure can be maintained between an ablation electrode and the heart wall.

Additional objects and features of the invention will appear from the following description from which the preferred embodiments are set forth in detail in conjunction with the accompanying drawings.

BRIEF DESCRIPTION OF THE DRAWINGS

FIG. 1 is a side elevational view of an apparatus for detecting contact pressure of the present invention.

FIG. 2 is an enlarged cross-sectional view of the apparatus shown in FIG. 1, taken along the line 2—2 of FIG. 1, engaging a portion of the wall of the heart.

FIG. 3 is a cross-sectional view taken along the line 3—3 of FIG. 2.

FIG. 4 is a cross-sectional view taken along the line 4—4 of FIG. 2.

FIG. 5 is a side elevational view, partially sectioned, of the distal extremity of another embodiment of an apparatus for detecting contact pressure of the present invention.

SUMMARY OF THE INVENTION

In general, the apparatus for detecting contact pressure of the present invention is used for performing an operation inside a body in the vicinity of a wall therein. The apparatus includes a flexible elongate member having proximal and distal extremities. The distal extremity is adapted to be inserted into the body for performing the operation therein and the proximal extremity is adapted to be disposed outside the body. Pressure sensor means is carried by the distal extremity of the flexible elongate tubular member for sensing the force being applied to the distal extremity in bringing it into engagement with the wall whereby the force being applied to the distal extremity can be controlled.

DETAILED DESCRIPTION

More in particular, a medical device of the present invention can be in the form of an apparatus 11 for mapping the wall of a chamber of the heart having blood therein of the type disclosed in U.S. Pat. No. 5,156,151 and copending application Ser. No. 08/044,255 filed Apr. 7, 1993. As disclosed therein and as illustrated in FIG. 1, endocardial mapping device or apparatus 11 includes a flexible elongate tubular member or shaft 12 formed of a suitable material such as plastic which is circular in cross section. Shaft 12 has a proximal extremity 13 adapted to be inserted into a human body for performing an operation in the body and a distal extremity 14 adapted to be disposed outside of the body to permit access to and operation of apparatus 11. A basket assembly 16 is carried by distal extremity 14 and is moveable between a contracted position and an expanded position.

Basket assembly 16 is provided with a plurality of longitudinally extending flexible arms 17 which have an outwardly bowed shaped memory for expanding the basket assembly into engagement with wall 18 of the heart as shown in FIG. 2. Arms 17 have proximal extremities or end portions 21 which are joined to distal extremity 14 of shaft 12 and distal extremities or end portions 22 which are joined at tip 23 of the basket assembly so that tip 23 is carried by shaft distal extremity 14. When expanded as illustrated in FIG. 1, arms 17 are circumferentially and symmetrically spaced-apart. A plurality of longitudinally spaced-apart electrodes 26 are carried by each arm 17 for engaging heart wall 18. The arms can also carry a plurality of longitudinally spaced-apart radiopaque markers or traces, not shown in the drawings, formed of a suitable material such as platinum or gold to permit fluoroscopic viewing of basket assembly 16.

Pressure sensor means in the form of pressure transducer 27 is carried by distal extremity 14 of shaft 12 for sensing the force being applied to the distal extremity in bringing it into engagement with heart wall 18. Transducer 27 includes a cylindrical housing 31 made of any suitable material such as brass or plastic and having proximal and distal end portions 32 and 33. Housing 31 is formed with an outer tubular wall 36 which is circular in cross section and an inner transverse wall 37 which separates proximal and distal cavities 41 and 42 provided in respective end portions 32 and 33. Tubular wall 36 has an outer diameter on the order of 0.070 to 0.120 inch. Tip 23 of basket assembly 16 is disposed in proximal cavity 41 and means for mounting housing 31 to the basket assembly includes a plurality of fibers 43, made from any suitable material such as Kevlar, interlaced between a plurality of circumferentially disposed bores 46 provided in the housing and distal end portions 22 of arms 17 (See FIGS. 2 and 3).

An electrical assembly 47 is disposed in distal cavity 42 of cylindrical housing 31 and includes a pressure transducer 27 providing an output signal reflecting the force being applied to distal extremity 14 and being transferred to transducer 27. Electrical assembly 47 includes a flex circuit 51 formed from a polyimide disk 52 which serves as a layer of insulating material and has a first surface disposed against planar transverse wall 37 and an opposite second surface 54 with conductive elements or lines disposed thereon and arranged in first and second patterns 56 and 57 (See FIG. 4). The lines of each pattern are formed from any suitable material such as copper disposed on disk 52 by either additive or subtractive techniques known to those skilled in the art and are interspersed with but do not connect to the lines of the other pattern. A second substrate or disk 61 made of any suitable material such as polyimide is included within electrical assembly 47 and has a layer 62 of conductive carbon filled epoxy silk screened or otherwise disposed thereon. Disk 61 is disposed in distal cavity 41 in juxtaposition with flex circuit 51 with carbon layer 62 overlying and in contact with lines 56 and 57. Circular disks 52 and 61 have a diameter ranging from 0.050 to 0.080 inch.

Although pressure transducer 27 has been shown and described with electrical assembly 47 therein, it should be appreciated that pressure transducers having other means for measuring changes in pressure can be provided and be within the scope of the present invention.

Transducer 27 includes a pressure transmissive tip or pad element 66 carried by housing 31 and made of any suitable pliable material such as silicone. The pad element has a rounded outer surface 67 for engaging heart wall 18 and an annular groove 68 around the middle thereof. Housing 31 is formed with a flange 71 around the end of distal end portion 33 which extends inwardly into groove 68 for securing the pad element to the housing. First and second leads or wires 72 and 73 are connected to respective lines 56 and 57 and extend through a bore in transverse wall 37 into an arm 17 and shaft 12 for electrically connecting electrical assembly 47 with proximal extremity 13 of the shaft.

A handle 81 is joined to proximal extremity 13 of shaft 12 for operating endocardial mapping apparatus 11. A connector 82 is included on handle 81 and is electrically connected to wires 72 and 73 and pressure transducer 27. Connector 82 permits apparatus 11 to be connected to a control console 83 as shown in FIG. 1 for operation thereof. The control console includes a power supply and an amplifier circuit (not shown) for sending a signal to the pressure transducer and for amplifying the signal received from the pressure transducer, respectively, and a measurement circuit (also not shown) for receiving the information from the pressure transducer and displaying it to a meter 86 and/or a digital display 87.

In operation and use, endocardial mapping apparatus 11 is introduced into a chamber of a heart, as for example the ventricle of the heart, in a manner similar to that described in U.S. Pat. No. 5,156,151 and copending application Ser. No. 08/044,255 filed Apr. 7, 1993 for performing an operation in the vicinity of heart wall 18. More specifically, as apparatus 11 is advanced down to the apex of the ventricle, pressure transducer 27 engages heart wall 18 so as to permit the axial force being applied to handle 81 and the related contact pressure of distal extremity 14 against the heart wall to be sensed by the pressure transducer. The sensed force is transmitted to disk 61 of electrical assembly 47 so as to cause carbon layer 62 overlying and in engagement with lines 56 and 57 to compress and decrease the electrical resistance of the carbon particles therein. This change in resistance alters the electrical signal being transmitted through pressure transducer 27 to control console 83.

The electrical signal received from pressure transducer 27 by control console 83 is processed thereby so that the forces or pressures between the heart wall and the pressure transducer are shown on meter 86 and/or display 87. Based upon this information, the operating physician can control the axial force being applied to apparatus 11 so as to keep it within a safe level and not puncture or otherwise damage heart wall 18. Once apparatus 11 has been properly positioned within the heart, electrodes 26 on arms 17 of expanded basket assembly 16 permit the mapping of electrical impulses on heart wall 18.

It should be appreciated that the apparatus and method of the present invention can have other applications on an endocardial mapping apparatus and be within the scope of the invention. For example, one or more pressure transducers could be mounted on arms 17 of apparatus 11 for measuring the contact pressure between the arms and electrodes 26 thereon and heart wall 18 during mapping and/or ablation. As another example and embodiment, a portion of a steerable catheter 96 of the type disclosed in copending application Ser. No. 07/894,529 filed Jun. 5, 1992 is illustrated in FIG. 5. Catheter 96 includes a flexible elongate tubular member or shaft 97 which is circular in cross section and has a proximal extremity (not shown) and a distal extremity 98. A contact pressure transducer 101 is carried by distal extremity 98.

Pressure transducer 101 is substantially similar to pressure transducer 27 and includes a generally cylindrical housing 103 made of any suitable material such as brass or plastic and having proximal and distal end portions 106 and 107. Distal portion 107 has an outer tubular wall 111 which is circular in cross section and a bottom wall 112 extending transversely within tubular wall 111 at right angles thereto. Proximal portion 106 includes a tubular boss or shank 113 which extends from bottom wall 112 coaxial with tubular wall 111 into shaft distal extremity 98. Shank 113 has a plurality of spaced-apart annular barbs 116 for securing housing 103 to the shaft.

Tubular wall 111 of distal end portion 107 forms a distal cavity 117 in housing 103. Pressure transducer 101 is provided with the same electrical assembly 47 described above and including flex circuit 51 with first and second patterns of conductive lines 56 and 57 and carbon layer 62 overlying lines 56 and 57. A pressure transmissive pad element 126 substantially identical to pad element 66 described above and having an annular groove 127 therearound is disposed within distal cavity 117 in engagement with electrical assembly 47. Pad element 126 is secured in distal cavity 117 by an inwardly extending flange 128 formed at the end of tubular wall 111 and sized for snug disposition within groove 127. First and second wires 131 and 132 are connected to respective patterns 56 and 57 of conductive lines and extend through a bore in bottom wall 112 into shaft 97 for electrically connecting electrical assembly 47 to the proximal extremity of steerable catheter 96.

Pressure transducer 101 includes an external tip or shell 136 made of any suitable conductive material such as platinum for serving as an ablation means and an electrode carried by shaft distal extremity 98. Shell 136 generally encapsulates housing 103, being generally tubular in configuration and having a rounded end 137 which extends over the rounded end of pad element 126 for engaging heart wall 18 and an opposite open end 138 which is swaged around bottom wall 112 for securing the shell to housing 103. Wires 141 extend through shaft 97 and are electrically connected to shell 136 for providing radio frequency energy to the shell during ablation as described in copending application Ser. No. 07/894,529 filed Jun. 5, 1992.

Shank 113 is longitudinally sized so that shaft distal extremity 98 is spaced from bottom wall 112 a sufficient distance to permit axial movement of shell 136 with respect to housing 103, as shown by a dotted lines in FIG. 5, upon engagement of the shell with heart wall 18. In this manner, the axial forces exerted by and upon shell 136 when it engages the heart wall are transmitted to pad element 126 so as to be reflected in the electrical signal across electrical assembly 47 as discussed above. It has been found that an axial movement of shell 136 on the order of 0.002 to 0.003 inch is sufficient to permit measurement of the contact forces thereon.

The proximal extremity of steerable catheter 96 can be provided with a handle similar to handle 81 described above for operating the catheter and a control console connected to the catheter and similar to console 83 described above for supplying power to pressure transducer 101 and displaying the signal received therefrom. The control console of catheter 96 would also include a radio frequency generator for providing energy to electrode shell 136 during ablation.

In operation and use, pressure transducer 101 provided at the distal extremity of steerable catheter 96 permits the axial force being applied by the operating physician to the catheter to be monitored and controlled. Based upon this information, the operating physician can maintain a minimum contact pressure during ablation so as to better ensure intimate contact between electrode shell 136 and the targeted tissue of heart wall 18 and avoid forming dangerous coagulation of the blood. It has been found to be necessary to maintain a minimum force on the order of 10 to 15 grams to obtain a good predictable lesion.

The apparatus and method of the present invention can also be applied to laparoscopic surgical instruments and for instruments for use in the treatment of aneurisms where the vessel wall is weak and thin and less capable of withstanding significant forces.

From the foregoing, it can be seen that several embodiments of the invention have been provided which can sense the amount of force being exerted by the distal extremity of a medical device against a wall within a body. In one of the embodiments shown, the axial force of an endocardial mapping device can be monitored. In another embodiment shown, a device and method are provided in which a desired minimum pressure can be maintained between an ablation electrode and the heart wall.

What is claimed is:

1. In an apparatus for performing a procedure in a chamber defined by a wall of a heart in a body in the vicinity of the wall, a flexible elongate member having proximal and distal extremities, the distal extremity being adapted to be inserted into the heart for performing the procedure therein and the flexible elongate member having a length so that the proximal extremity is disposed outside the body when the distal extremity is in the heart, the flexible elongate member having a column strength so that a force provided to the proximal extremity causes the distal extremity to engage the wall of the chamber, a pressure sensor carried by the distal extremity of the flexible elongate member and generating an electrical signal, electrical conductive means connected to the pressure sensor and extending to the proximal extremity, the pressure sensor included within means for sensing the pressure being applied by the distal extremity against the wall to ensure that a pressure sufficient to puncture the wall is not exerted on the distal extremity during the procedure.

2. The apparatus of claim 1 together with an ablation electrode carried by the distal extremity distal of the pressure sensor.

3. The apparatus of claim 2 wherein the ablation electrode is carried by the pressure sensor.

4. The apparatus of claim 1 wherein the pressure sensor means includes electrical means for adjusting an electrical signal to reflect the force being applied to the distal extremity.

5. The apparatus of claim 4 wherein the electrical means includes a layer of insulating material having a surface with first and second interspaced conductive elements carried thereby and a layer of carbon particles overlying the conductive elements.

6. A method for use with an apparatus having a flexible elongate member with proximal and distal extremities to dispose the distal extremity in a chamber defined by a wall of a heart in a body for performing a procedure in the vicinity of the wall comprising the steps of introducing the distal extremity of the flexible elongate member via a lumen into the chamber, applying a force to the proximal extremity of the flexible elongate member so that the distal extremity engages the wall, sensing the contact pressure of the distal extremity against the wall to obtain information regarding the magnitude of the contact pressure and utilizing the information to ensure that a force is not applied to the proximal extremity which is sufficient to cause the distal extremity to puncture the wall during the procedure.

7. The method of claim 6 together with the step of sensing electrical impulses from the wall.

8. The method of claim 6 together with the step of performing ablations in the wall.

9. In an apparatus for use for ablation in a wall of a heart in a body of a patient, a flexible elongate member having proximal and distal extremities, the distal extremity being adapted to be inserted into the body and the flexible elongate member having a length so that the proximal extremity is disposed outside the body when the distal extremity is in the heart, an ablation electrode formed of a conductive material adapted to engage the wall mounted on the distal extremity of the flexible elongate member, conductive means connected to the ablation electrode and extending to the proximal extremity, pressure sensing means mounted in the distal extremity of the flexible elongate member and sensing the pressure being applied by the ablation electrode to the wall whereby it can be ascertained whether the ablation electrode is in intimate contact with the wall of the heart and also ascertained that the pressure exerted on the wall of the heart is insufficient to puncture the surface of the wall of the heart, the pressure sensing means creating an electrical output and electrical conductive means connected to the pressure sensing means and extending to the proximal extremity.

10. The apparatus of claim 9 wherein the pressure sensing means includes electrical means for adjusting the electrical output to reflect the pressure force being applied by the ablation electrode to the wall.

11. The apparatus of claim 10 wherein the electrical means includes a layer of insulating material having a surface with first and second interspaced conductive elements carried thereby and a layer of carbon particles overlying the conductive elements.

12. The apparatus of claim 9 wherein the conductive material of the ablation electrode extends around the distal extremity.

* * * * *